United States Patent [19]
Kubisiak et al.

[11] Patent Number: 5,331,177
[45] Date of Patent: Jul. 19, 1994

[54] TURBIDITY SENSOR WITH ANALOG TO DIGITAL CONVERSION CAPABILITY

[75] Inventors: David Kubisiak, Carver County; Mark L. Wilson, Ramsey County, both of Minn.

[73] Assignee: Honeywell Inc., Minneapolis, Minn.

[21] Appl. No.: 53,042

[22] Filed: Apr. 26, 1993

[51] Int. Cl.$^5$ ............................................. G01N 15/06
[52] U.S. Cl. ..................................... 250/574; 250/575
[58] Field of Search ............... 250/573, 574, 575, 576; 356/339, 341, 440, 441, 442; 73/61.48, 61.69, 293, 323; 340/619

[56] References Cited

U.S. PATENT DOCUMENTS

| | | | |
|---|---|---|---|
| 4,193,692 | 3/1980 | Wynn | 356/341 |
| 4,619,530 | 10/1986 | Meserol et al. | 356/440 |
| 4,659,218 | 4/1987 | de Lasa et al. | 250/574 |
| 4,906,101 | 3/1990 | Lin et al. | |
| 4,999,514 | 3/1991 | Silveston | |
| 5,048,139 | 9/1991 | Matsumi | |
| 5,059,811 | 10/1991 | King et al. | |
| 5,099,123 | 3/1992 | Harjunmaa | |
| 5,104,228 | 4/1992 | Baillie | |
| 5,140,168 | 8/1992 | King | |
| 5,163,202 | 11/1992 | Kawakami et al. | 250/574 |
| 5,164,604 | 11/1992 | Blair et al. | 250/574 |

OTHER PUBLICATIONS

Article–May, 1993 issue of Sensors Magazine entitled "Σ-Δ Modulator Interfacing With Silicon Microsensors".
Article from Jul. 1993 Sensors Magazine entitled "A New RISC-Based Data Acquisition System".
Catalog Reproduction from Crystal Semiconductor Corp. Jan. 1989, AN10REV1.

*Primary Examiner*—David C. Nelms
*Assistant Examiner*—K. Shami
*Attorney, Agent, or Firm*—William D. Lanyi

[57] ABSTRACT

A turbidity sensor is provided with a light source and a plurality of light sensitive components which are disposed proximate a conduit to measure the light intensity directly across the conduit from the light source and at an angle therefrom. The conduit is provided with a plurality of protrusions extending radially inward from the walls of the conduit to discourage the passage of air bubbles through the light beam of the sensor. The direct light beam and scattered light are compared to form a relationship that is indicative of the turbidity of the liquid passing through the conduit. The rate of change of turbidity is provided as a monitored variable.

14 Claims, 7 Drawing Sheets

SECTION III - III

TURBIDITY SENSOR WITH ANALOG TO DIGITAL CONVERSION CAPABILITY

BACKGROUND OF THE INVENTION

1. Field of the Invention

The present invention relates generally to turbidity sensors and, more particularly, to a turbidity sensor which is configured to decrease the adverse affect that can result from air bubbles in a stream of fluid whose turbidity is to be determined and, in addition, is provided with the capability of determining the rate of change of turbidity as a function of time to enable an appliance to make various energy and time saving decisions.

2. Description of the Prior Art

Turbidity has been defined, by the American Public Health Association, as an expression of the optical property that causes light to be scattered and absorbed rather than transmitted in straight lines through a fluid. Therefore, turbidity is generally measured as the ratio of scattered light to directly transmitted light. This can be interpreted as a measure of the relative clarity of a liquid. It should be understood that turbidity is not a direct measurement of suspended particles in fluid but, instead, is a measurement of the scattering effect that suspended particles have on light. The amount and color of light that is scattered by particles suspended in a fluid is dependent on the size, shape, composition and refractive index of the particles.

A light beam will pass through pure water while remaining relatively undisturbed. If solids are suspended in the water, they interfere with the light transmittance through the water in a way which is related in a way to the type of particle and the wavelength of the incident light. A minute particle interacts with the light by absorbing the energy of the light and then reradiating the light energy in all directions. This scattered light depends on the ratio of particle size to the wavelength of the incident light.

During the first few years of this century, early attempts to quantify turbidity were made. A standard suspension fluid using 1000 ppm of diatomaceous earth in distilled water was used and dilutions of the reference suspension fluid resulted in a series of standard suspensions that were used to derive a ppm silica scale for calibrating the contemporary turbidimeters. These devices typically consisted of a flat bottomed glass tube and a special candle. Measurements were made by slowly pouring a turbid sample into the tube until the visual image of the candle, when viewed from the open top of the tube, defused to a uniform glow. This was called the extinction point and, although this method was very subjective, trained workers achieved remarkably consistent results. Modern turbidity sensors utilize a light source and one or more light sensitive components. Typically, the light source and light sensitive components are disposed around the outer periphery of a transparent conduit through which a fluid is caused to flow. One light sensitive component is placed directly across the conduit from the light source on a common diameter. The other light sensitive component is disposed at a 90° degree offset from both the light source and the other light sensitive component. The first light sensitive component, which is placed opposite to the light source on a common diameter, is intended to receive light emanated directly from the light source. The second light sensitive component is intended to receive light scattered by particulate matter within the fluid flowing through the conduit. A ratio of the intensities of light received by the two light sensitive components can be used as a measurement of the fluid's turbidity. Many different types of fluidity sensors are known to those skilled in the art.

U.S. Pat. No. 5,140,168, which issued to King on Aug. 18, 1992, discloses a turbidimeter signal processing circuit that uses alternating light sources. The turbidimeter includes a housing having a cavity with an inlet through which a fluid flows. Two emitters are alternately driven by an alternating signal having a given frequency to transmit modulated light beams through the fluid. Two detectors produce signals representing the intensity of scattered and unscattered light within the fluid. Each of these detector signals is processed to measure the level of the signal component at the given frequency. Such processing includes filtering and phase demodulating the detector signals to produce a signal indicative of the levels of the component signals at the given frequency. The turbidity is calculated from the signal levels measured as each emitter is excited.

U.S. Pat. No. 5,104,228, which issued to Baillie on Apr. 14, 1992, describes a photosensitive turbidimeter with a nonfouling measurement chamber. The turbidity of liquids, including oil contaminated water, may be measured by an apparatus having a first elongated shell member defining a turbid liquid measurement chamber and opposed head members forming windows for transmitting a light beam through the measurement chamber between a light source and a photosensitive element. A second shell member is disposed around the first shell member and defines with the first shell member and the opposed head members clear liquid supply chambers for supplying a clear liquid to wash over the windows and prevent contact of the turbid liquid with windows during operation of the apparatus. A flow of clear liquid, such as water, may be controlled by a pump and a throttling valve with orifices in each flow line to limit the flow of clear liquid. A mixture of clear liquid and turbid liquid is discharged from the turbidity measurement chamber into a discharge manifold formed between the shell members.

U.S. Pat. No. 5,099,123, which issued to Harjunmaa on Mar. 24, 1992, describes a method for determining by absorption of radiations the concentration of substances in absorbing and turbidmatricies. The method and apparatus for noninvasively testing analytical substances in turbid matrices comprises a sample which is irradiated with a beam of electromagnetic energy at two alternating wavelengths at which the absorption by the background is the same at one of which the radiation is absorbed by the analyte and at the other is not. The apparatus comprises means which enable the control of an input energy at the two wavelengths so that at the output from the sample the electrical signals issuing after detection cancel in the absence of the analyte in the sample. When analyte is present cancellation no longer occurs and a signal proportional to the analyte concentration in the sample is produced. The apparatus is also designed for shifting the response to zero when a calibrating known concentration of analyte is used as a standard, thus providing a controllable zeroing base line.

U.S. Pat. No. 5,059,811, which issued to King et al on Oct. 22, 1991, discloses a turbidimeter having a baffle assembly for removing entrained gas. The turbidimeter includes a housing with a cavity having an inlet through which the fluid enters the bottom of the cavity and an outlet through which the fluid exits the top of the cavity. A removable baffle assembly is located within the cavity between the inlet and the outlet. The baffle assembly is formed by three vertical plates which are spaced from each other and extending across substantially the entire cross sectional area of the cavity. The first plate defines a first passage near the top of the cavity through which all of the fluid entering the cavity must flow. The second and third walls define a second passage near the top of the cavity through which gas bubbles entrained in the fluid travel to the outlet. A third passage is defined between the first wall and the outlet and a mechanism is provided for measuring the turbidity of the fluid flowing through the third passage. A calibration device formed by a block of glass ceramic material is insertable in the third passage to simulate of known turbidity fluid.

U.S. Pat. No. 5,048,139, which issued to Matsumi on Sep. 17, 1991, discloses a washing machine with a turbidimeter and a method of operating the turbidimeter. The washing machine uses a turbidimeter to measure turbidity of cleaning water for controlling the duration of its washing and cleaning cycles. Quality of this control is improved by taking measurements when the water flow is weak, so that the effects of foams are negligible, and waiting until turbidity drops at the beginning of the cycle to detect the initial value used in subsequent steps. Sensitivity of the turbidimeter is automatically adjusted for accuracy when the operation is temporarily stopped and restarted during a cycle.

U.S. Pat. No. 4,999,514, which issued to Silveston on Mar. 12, 1991, discloses a turbidity meter parameter selection and waiting. The meter has a sensor unit supported in a fluid under test with a light source and at least two light sensors supported so that one light sensor is in line with the source to receive transmitted light and the remaining sensor or sensors are arranged to receive light scattered by the fluid. Both the source and sensors have flow forming chambers connected to a source of pressurized fluid so that a thin layer of this fluid is caused to flow over lenses of the source and sensors to prevent deposition of material from the fluid under test. The signals from the sensors are digitized and the intensity of the source is digitally controlled to maintain at least one of the sensor signals within a suitable range, thus enabling operation over a wide range of turbidities and automatic selection of turbidimetric and nephelometric modes of operation as appropriate.

U.S. Pat. No. 4,906,101, which issued to Lin et al on Mar. 6, 1990, describes a turbidity measuring device for measuring turbidity in static or dynamic streams wherein the fluid has up to 8500 ppm solids and at depth of up to 8 inches. The device contains a high intensity light source, means for controlling the wavelength of the transmitted light to between 550 and 900 nanometers to filter out color variables in the streams. It also contains a very sensitive photosensor aligned with the viewing means for picking up the light transmitted through the streams.

Turbidity sensors can be used in modern home appliances, such as dishwashers, to monitor the progress of cleaning cycles. The turbidity of the water in a dishwashing machine or clothes washing machine can provide an important indication of the efficacy of the cleansing process. It has been determined that the use of a turbidity sensor can be adversely affected by the presence of air bubbles in the fluid stream being monitored. If, for example, an air bubble lodges at a position on the inner cylindrical surface of a conduit proximate a light sensitive component, the bubble could block the passage of light to the light sensitive component and seriously distort the sensor's ability to accurately determine the turbidity of the fluid flowing through the conduit.

SUMMARY OF THE INVENTION

The present invention addresses several problems that currently exist with regard to the sensing of turbidity. It provides a means for determining the turbidity of a fluid as a function of two light intensity values which represent direct and scattered light paths. In addition, it combines the light intensity values in a way which permits a general linearization of the results. The resultant turbidity value can be used as an absolute indication of turbidity or, alternatively, can be used as an index to select a turbidity value from a table in the memory of a microprocessor system. In addition, the present invention provides a plurality of protrusions, or dimples, formed in the wall of a conduit through which the fluid is flowing. The purpose of the dimples is to discourage the passage of air bubbles proximate the light source or light sensitive components of the turbidity sensor. By discouraging the passage of bubbles proximate these components, the present invention avoids distortions in the turbidity calculations that could otherwise occur.

In a preferred embodiment of the present invention, a turbidity sensor is provided with a light source such as a light emitting diode. In addition, first and second light sensitive components are disposed in light communication relation with the light source. The first light sensitive component is disposed to receive light directly emanating from the light source and the second light sensitive component is disposed to receive light emanating from the light source and scattered by particles suspended between the light source and the first light sensitive component. The first and second light sensitive components have first and second output signals, respectively, which are representative of the light intensity received by the respective light sensitive components. The present invention provides a means for determining a predefined relationship of the first and second output signals. This relationship can be a ratio or a more complicated mathematical relationship which results in a value that can be used as a representation of the turbidity of a fluid sample. The turbidity sensor in a preferred embodiment of the present invention also comprises a conduit that is shaped to conduct a fluid therethrough. The light source and the first and second light sensitive components are disposed proximate a wall of the conduit for communication of light through a fluid that flows within the conduit. A plurality of protrusions are formed in the wall of the conduit and extend inwardly into the conduit. The light source is disposed proximate one of the protrusions, the first light sensitive component is disposed proximate another protrusion and the second light source is disposed proximate a third protrusion. In a preferred embodiment of the present invention, a microprocessor is used to determine the predefined relationship between the first and second output signals and to perform the necessary mathematical operations to provide a generally linearized value of turbidity based on the two signals from the light sensitive components. In addition, the microprocessor can also be used to determine a rate of change of turbidity in the sampled fluid. The turbidity value determined by the microprocessor can be compared to a preselected threshold magnitude.

The turbidity sensor of the present invention provides a means for passing a fluid between the light source and the two light sensitive components. In one particularly preferred embodiment of the present invention, the light source and the two light sensitive components are disposed on an outer cylindrical surface of a conduit and directed inwardly toward the center of the conduit. A portion of the wall of the conduit is transparent to the light provided by the light source. In addition, the light providing and light receiving components are disposed within protrusions formed in the wall of the conduit.

BRIEF DESCRIPTION OF THE DRAWINGS

The present invention will be more fully understood from a reading of the Description of the Preferred Embodiment in conjunction with the drawings, in which.

DESCRIPTION OF THE PREFERRED EMBODIMENT

Figure 1:
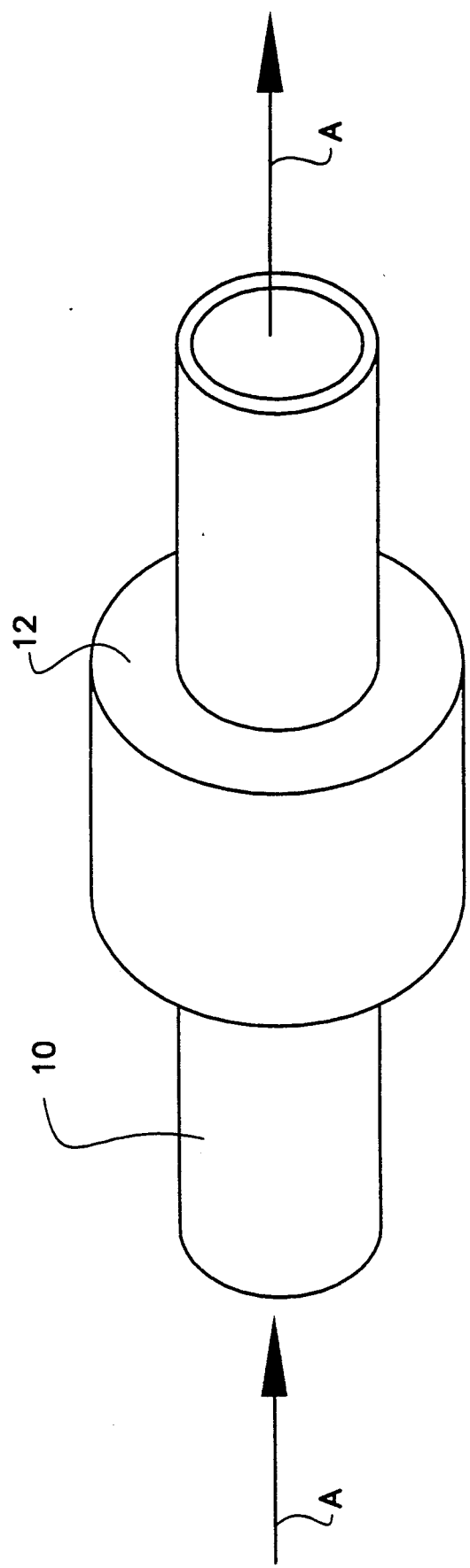
FIG. 1 illustrates one embodiment of the present invention.

Throughout the Description of the Preferred Embodiment of the present invention, like reference numerals will be used to identify like components.

FIG. 1 shows the general outer configuration of a turbidity sensor made in conformance with the present invention. A conduit 10 is shaped to permit the flow of a fluid therethrough in the directions represented by arrows A. Around an outer periphery of the conduit 10, an annular electronics package 12 is disposed. The electronics package 12 comprises the necessary components to provide a light source and one or more light sensitive components directed to pass a light beam through the wall of the conduit 10 and through the fluid passing therethrough. Several different types of turbidity sensing arrangements are known to those skilled in the art. For example, a single light source can be associated with two light sensitive components which are placed at locations to receive light directly emanating from the light source and light which is scattered by particulate matter within the fluid stream. Alternative configurations use two light sources and a single light sensitive component to perform a similar function. In this type of arrangement, the light sources are modulated in such a way that they are not both energized at the same time. Appropriate circuitry is provided to synchronize the receipt of light signals by the light sensitive component with the transmission of light from the two light sources. It should be understood that the particular arrangement of light sources and light sensitive components is not a restricting characteristic of the present invention.

Figure 2:
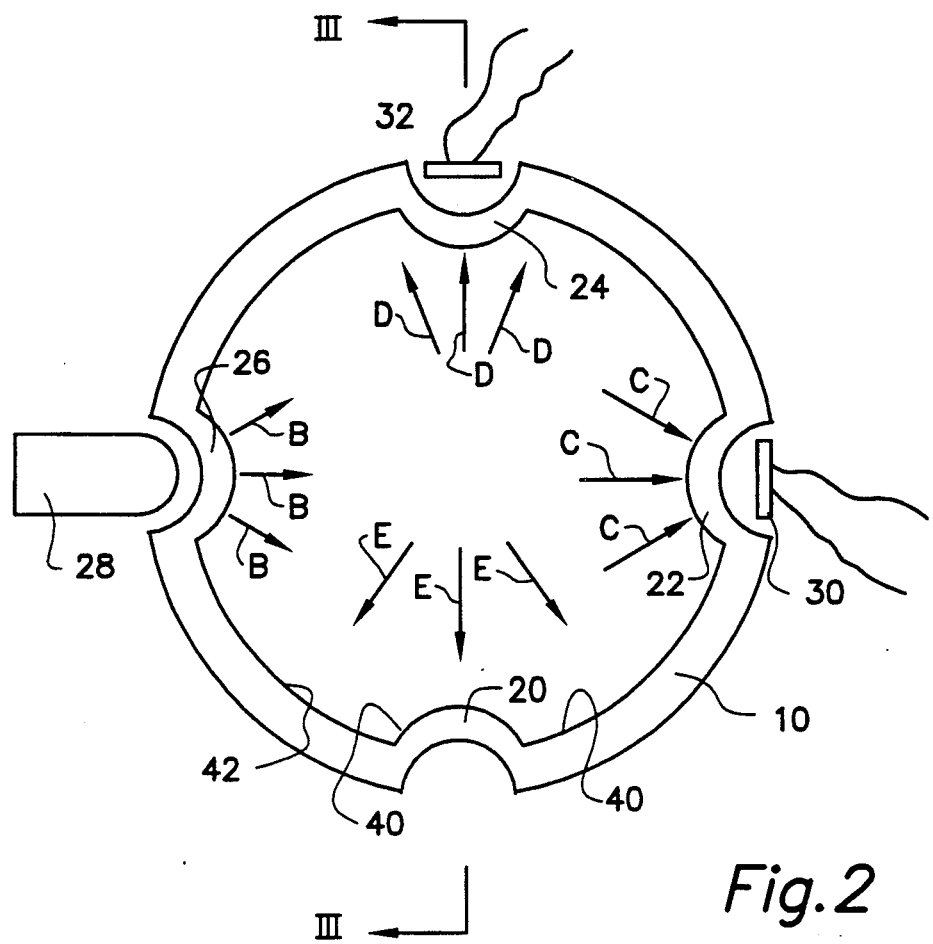
FIG. 2 illustrates a sectional view of a conduit with a light source and two light sensitive components associated therewith.

FIG. 2 shows a section view of the conduit 10. The wall of the conduit 10 is provided with a plurality of protrusions, 20–26, formed therein. Each protrusion, or dimple, is formed in the wall in such a way that it extends radially inwardly toward the center of the conduit 10. In a preferred embodiment of the present invention, the light source 28 is disposed proximate one of the protrusions 26 and the two light sensitive components, 30 and 32, are disposed in two other protrusions, 30 and 24, respectively. Although not shown in FIG. 2, the annular housing 12 described above in conjunction with FIG. 1 would be disposed around the light source 28 and the light sensitive components, 30 and 32, and would also contain the necessary electronic components to provide a sensing circuit associated with the components shown in FIG. 2. In addition, the annular housing 12 could also comprise a microprocessor to perform some of the mathematical operations relating to the determination of a turbidity value as a function of the light intensity received by the two light sensitive components.

With continued reference to FIG. 2, light emanates from the light source 28 as indicated by arrows B. This light source 28 can be a light emitting diode, or LED, which is commercially available from many different sources. Some of this light passes diametrically across the conduit and is received by the light sensitive component 30 as indicated by arrows C. If the fluid passing through the conduit 10 is very clear and contains a very low amount of particulate matter, most of the light emanating from the light source 28 will pass through the fluid directly to the light sensitive component 30. If, on the other hand, the fluid passing through the conduit 10 contains a large amount of particular matter, a significant portion of the light emanating from the light source 28 will be scattered by the suspended particulate matter and will pass toward the light sensitive component 32 as indicated by arrows D. Some of the light will also be scattered by the particulate matter in the direction represented by arrows E.

In FIG. 2, four protrusions are shown in the wall of the conduit 10 while only three components are disposed in protrusions. Protrusion 20 is empty in the illustration, but it should be understood that this additional protrusion could be used for other purposes. A temperature sensitive component can be disposed in protrusion 20 to provide a measurement of the temperature at precisely the same location where the turbidity is being monitored. In addition, an additional light sensitive component could be disposed in protrusion 20 as a means for providing a redundant measurement for light sensitive component 32. It should be understood that the wall of conduit 10 is transparent at the region of the protrusions to permit light to pass from the light source and toward the light sensitive components without interference from the material of the conduit 10.

Figure 3:
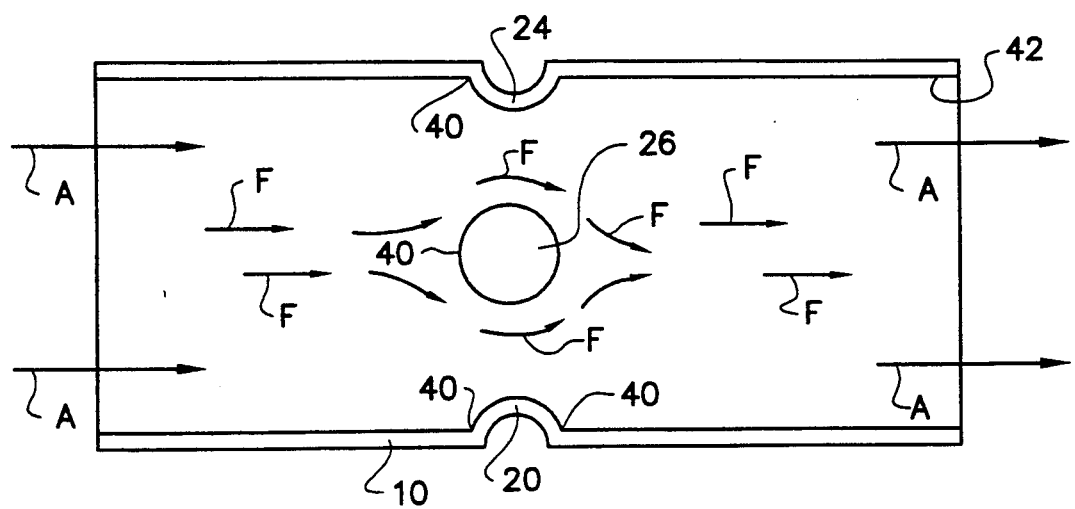
FIG. 3 illustrates a sectional view of the illustration shown in FIG. 2.

FIG. 3 is a sectional view of the illustration shown in FIG. 2. In FIG. 3, the light source and the light sensitive components are not shown. The purpose of FIG. 3 is to illustrate the advantage provided by the protrusions, 20-26, illustrated in FIG. 2. As fluid flows through the conduit 10 in the direction represented by arrows A, air bubbles can be entrained within the moving fluid and pass with it through the conduit. If an air bubble passes between the light source 28 and either one of the two light sensitive components, the presence of the air bubble in the light path between the components can adversely affect the magnitude of light received by the affected light sensitive component. The protrusions discourage the passage of bubbles in front of the light source and the light sensitive components. To illustrate this characteristic, arrows F represent the path along which air bubbles would pass in contact with the inner cylindrical surface of the conduit 10. The force of the fluid's movement through the conduit along arrows A cause the bubbles to migrate through the conduit while maintaining contact with the inner cylindrical surface of the wall of the conduit. Eventually, the bubbles would be expected to pass directly proximate the light source or the light sensitive components and possibly block the light path therebetween. If the migrating air bubbles move into contact with the region, identified by reference numeral 40 and located at the interface of the generally spherical surface of the protrusions and the generally cylindrical inner surface 42 of the conduit 10, the bubbles find an easier path around the spherical protrusion than over it. In other words, the bubbles tend to maintain their contact with the inner cylindrical surface 42 and refrain from moving onto the hemispherical surface of the protrusion which would require that the bubbles move radially inward toward the center of the conduit 10. This tendency of the air bubbles to pass around the protrusions keep them from passing through the light path through which light passes toward the two light sensitive components. This distortion of the bubbles path, as indicated by arrows F in the region of protrusion 26, prevent distortions from occurring in the receipt of light by the light sensitive components and the incorrect turbidity determinations that would result from these distortions.

The use of a plurality of light sensitive components in association with a light source permits a turbidity sensor to provide a value that represents the turbidity of a fluid. This value could be compared to threshold magnitudes to determine whether or not a fluid sample is greater than or less than a predetermined turbidity limit. The turbidity value of a fluid can also be used advantageously in certain applications such as home appliances. For example, if a time-based component, such as a microprocessor, is used to monitor the change in turbidity of a fluid, the rate of change of turbidity can be used as a valuable indication of the efficacy of a washing cycle. For example, if the turbidity is rapidly increasing, it might be presumed that the washing cycle is highly effective in removing dirt from dishware or clothes, depending on the appliance. If, on the other hand, a predetermined period of time elapses without a measurable increase in the turbidity of the monitored fluid, it might be presumed that the washing cycle is no longer effective in removing additional soil from the items being cleansed. This could be interpreted as an indication that both time and energy were being wasted by a continuation of the wash cycle. Although it should be recognized that different types of algorithms could be derived by those skilled in the art for maximizing the efficiency of wash and rinse cycles in major appliances, it should be recognized that the ability of a turbidity sensor to provide this type of information can lead to significant savings in both time and energy consumption. The rate of change of turbidity can be monitored for other purposes which also can save energy.

Figure 4:
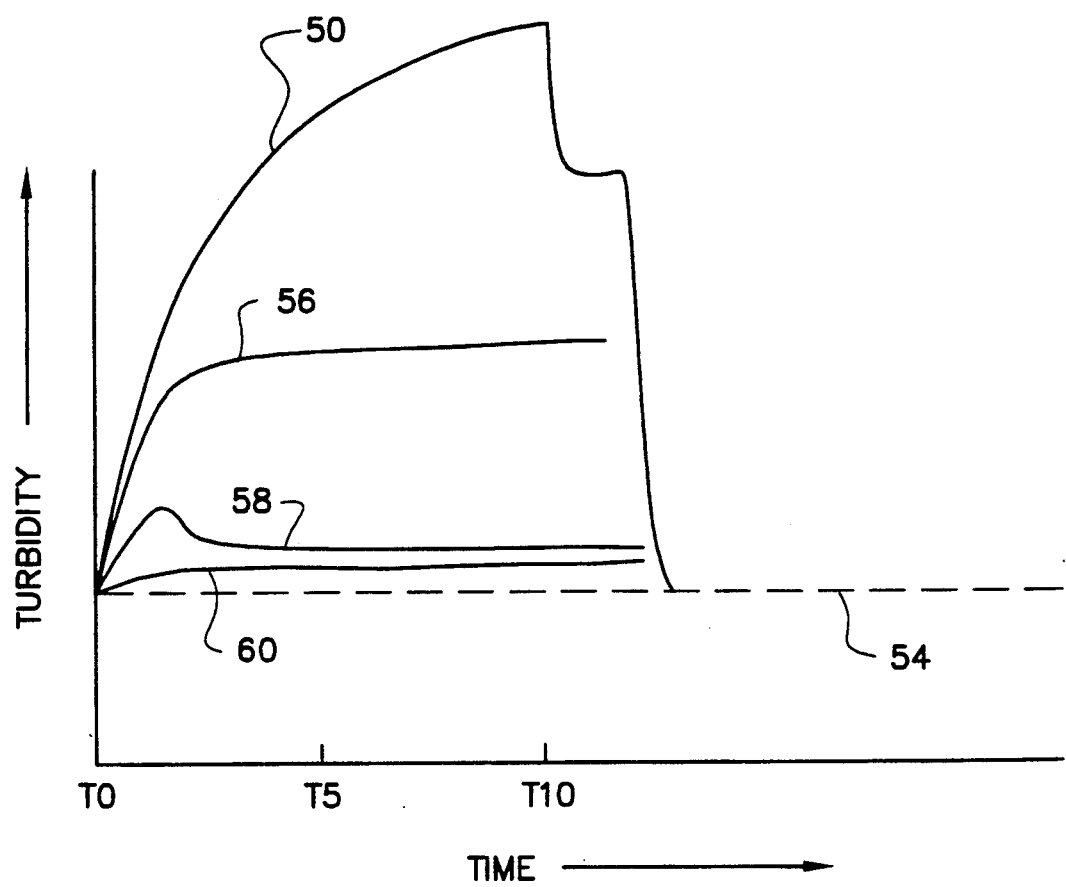
FIG. 4 shows the relationship between turbidity and time for several hypothetical conditions.

As shown in FIG. 4, the change in turbidity value as a function of time can very significantly depending on the circumstances associated with the turbidity measurement. For example, curve 50 is a hypothetical representation of the turbidity monitored in a dishwasher in which the dishes are heavily soiled with food that has been baked on the surfaces of the dishes. As the wash cycle continues from time T0 to time T10 the level of turbidity continues to rise although the rate of increase is decreasing as a function of time. This is an indication that the amount of soil removed from the dishes is not as great between times T5 and T10 as it was between times T0 and T5. Curve 50 also can be monitored to indicate other changes in the washing cycle. For example, the rapid decline in turbidity measurement which occurs immediately after time T10 can be an indication that either the temperature of the water was significantly increased to affect the solubility of particulate matter in the water or, alternatively, a significant amount of clean water was added to the original water circulating through the appliance. The subsequent decrease in turbidity value indicated by curve 50 where the value drops to the clear air magnitude represented by dashed line 54, illustrates that the fluid has been flushed from the appliance.

With continued reference to FIG. 4, curve 56 hypothetical represents a situation where dishes are soiled with small but greasy food particles. As can be seen, the turbidity value represented by curve 56 quickly rises at the initial portion of the cycle, but reaches a generally constant magnitude before time T5 and maintains that magnitude. This indicates that no additional particulate matter is being cleaned from the dishes. In a typical application of a turbidity sensor, the characteristics represented by curve 56 would indicate either that the dishes are as clean as they can be made or, alternatively, that the water temperature must be raised to effectively remove the grease from the dishes.

With continued reference to FIG. 4, curve 58 represents a hypothetical situation where the dishwasher cycle has begun with detergent, but with dishes that have already been cleaned. This could result from an accidental initiation of a dishwasher cycle on the belief that the dishwasher was full of dirty dishes. The extremely low magnitude of turbidity represented by curve 58 indicates that virtually no dirt is being removed from the dishes and, additionally, that the only turbidity being sensed in the water is that caused by the presence of dishwasher detergent particles. This type of indication could be used by a smart dishwasher to abort the cycle and save the energy that would otherwise be wasted. Curve 60 in FIG. 4 represents a hypothetical situation in which food is baked on the dishes and very little is removed during the washing cycle. As mentioned above, dashed line 54 represents the reading that a turbidity sensor would provide if only air existed between the light source and the light sensitive components.

Although FIG. 4 represents only a few hypothetical examples of how turbidity measurement can assist in the operation of a smart dishwasher, they show that the rate of change of turbidity can be an important indication of the operation of the appliance. If a microprocessor is used in association with the turbidity sensor, many different types of turbidity-time profiles can be stored in the memory of the microprocessor and the sensor can take appropriate action based on the occurrence of a known turbidity-time profile. The actions taken in response to these profiles can save significant time and energy that would otherwise be wasted.

Figure 5:
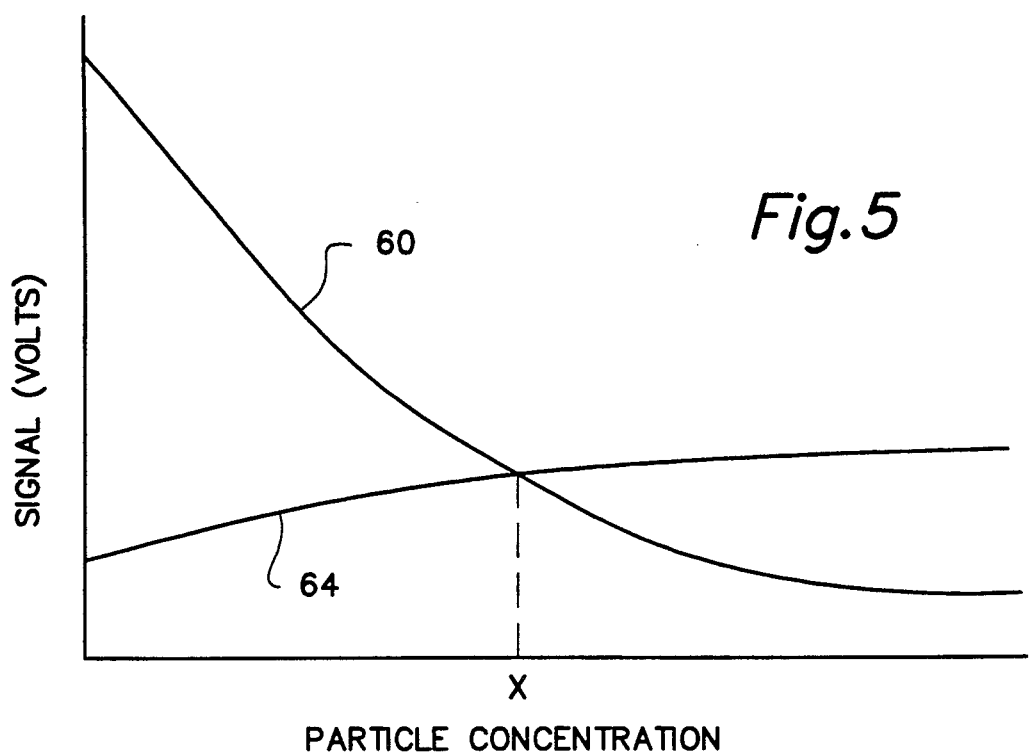
FIG. 5 shows the relationship between light emanating directly from a light source to a light sensitive component and scattered light received by another light source.

FIG. 5 is an exemplary graphical representation of the magnitude of signal received by the two light sensitive components described above. The first light sensitive component, which is disposed directly across the diameter of the conduit from the light source, receives light directly from the light source. The intensity of the light received by the first light sensitive component is illustrated as a function of particle concentration in FIG. 5. This representation is identified by reference numeral 60. The intensity of light received by the light sensitive component disposed at 90° degrees from the line between the first light sensitive component and the light source and positioned to receive scattered light is illustrated by curve 64 in FIG. 5. As can be seen, the intensity of light received directly from the light source decreases as a function of particle concentration in the fluid while the intensity of scattered light received increases as a function of the amount of particle concentration. As a point of reference, the value of particle concentration at which the two light intensities are equal is represented by an X in FIG. 5.

Figure 6:
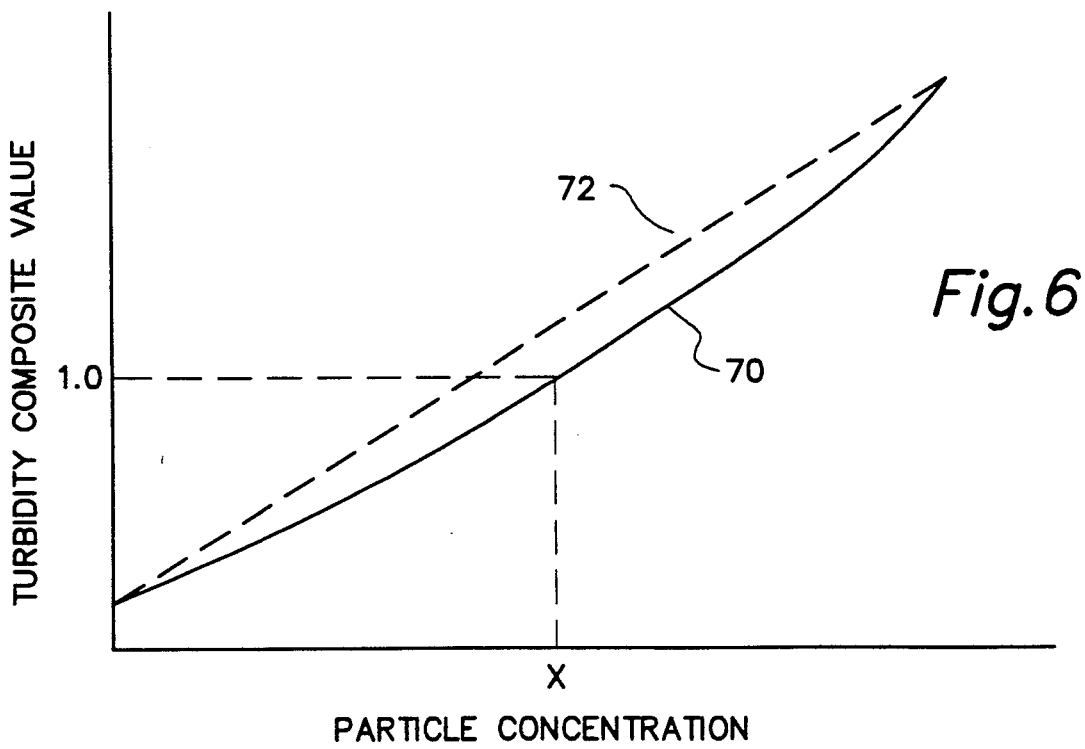
FIG. 6 shows the relationship between a turbidity component value and particle concentration in a fluid.

FIG. 6 illustrates a representation of turbidity composite value plotted as a function of particle concentration. The turbidity composite value can be formed in several ways within the scope of the present invention. One simple way of forming this composite value is to calculate a ratio of the scattered light to the direct light. In other words, the value of curve 64 divided by the value of curve 60 is represented by curve 70 in FIG. 6. Dashed line 72 is provided to show that curve 70 is not perfectly linear, but is sufficiently linear for many applications. The magnitude of particle concentration identified by an X in FIG. 6 is the same as that identified by an X in FIG. 5 and represents a turbidity composite value of 1.00 because of the identity between the magnitudes of curves 60 and 64 at that point. It should be understood that, based on the characteristics of the appliance in which the turbidity sensor is used, different mathematical representations can be used to provide a more linear relationship between a preselected calculated value and the turbidity of the fluid being monitored. In addition, the composite value represented in FIG. 6 can be scaled to provide an index of a stored table of values. An advantage of this technique is that it permits the values in the table to be changed for different applications of the turbidity sensor. For example, if water is being monitored, a first set of data can be included in the table. On the other hand, if a different fluid is being monitored, a different set of data can be stored in the table. In order to utilize this index technique in conjunction with a look up table, the magnitude of the turbidity composite value would normally be multiplied by some scaling factor, such as 100. This would permit the calculated composite value to be used directly as an integer look up index in conjunction with a table of turbidity values.

Figure 7:
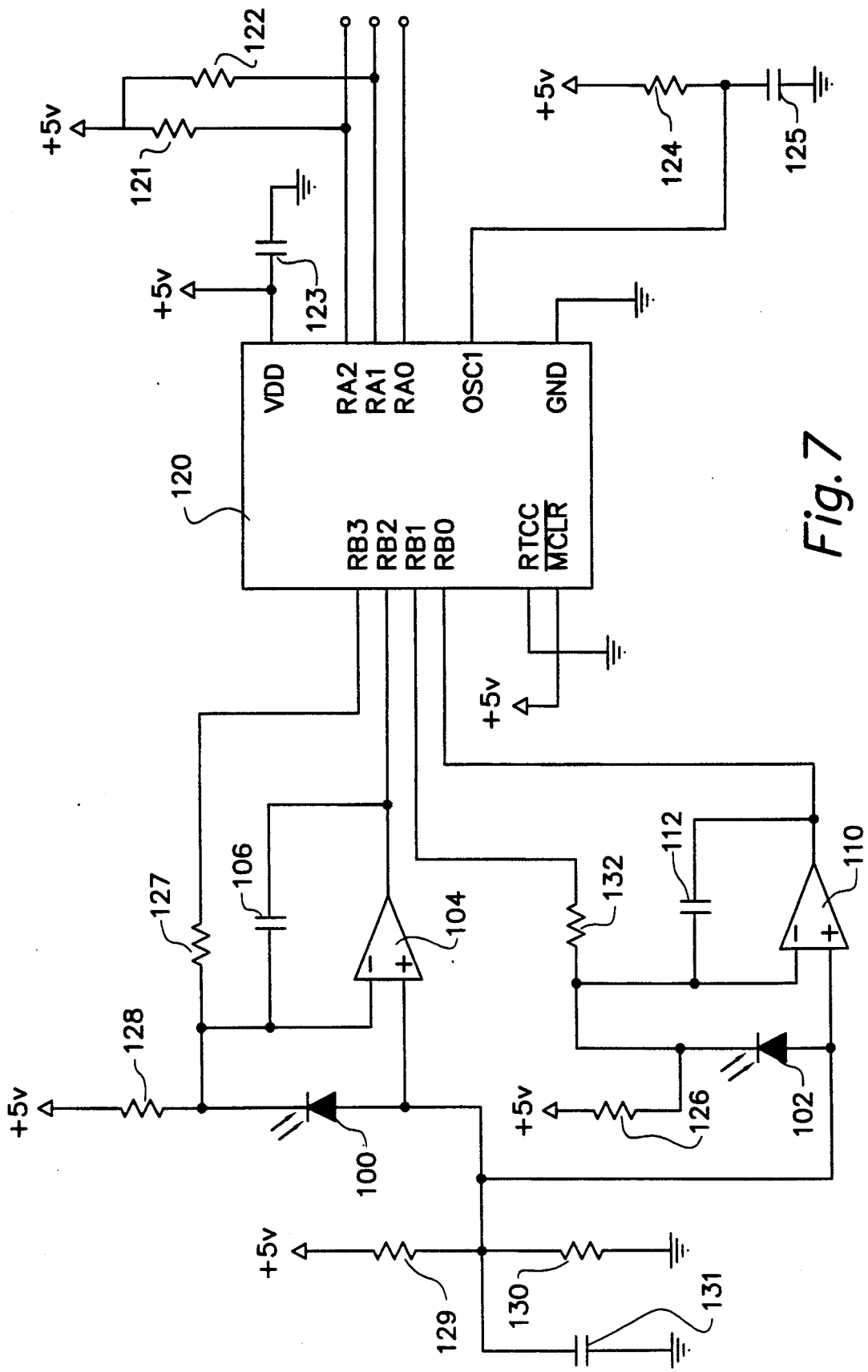
FIG. 7 shows the circuit used in a preferred embodiment of the present invention.

FIG. 7 shows a circuit that can be used in a preferred embodiment of the present invention. The light sensitive component disposed to receive the directly transmitted signal from the light source, such as a light emitting diode which is available in commercial quantities from Sharp, is identified by reference numeral 100 and the light sensitive component used to receive the scattered light signal is identified by reference numeral 102. The signal from photodiode 100 is connected to the noninverting input of operational amplifier 104 which is arranged with a capacitive feedback provided by capacitor 106. Similarly, the photodiode 102 is associated with operational amplifier 110 and capacitor 112 as shown.

The technique used by a preferred embodiment of the present invention, in conjunction with the RB0 and RB2 inputs and the RB1 and RB3 outputs of the microprocessor 120, is referred to as the delta-sigma method of analog to digital conversion. The delta-sigma method of analog to digital conversion used by the present invention involves the cancellation of the average signal current from the photodiode with a switched source current or charge. Current from the photodiode drives the integrator which comprises the operational amplifier and the feedback capacitor. The output is compared with a fixed voltage which is used as an input trip voltage of the microprocessor. Depending on the state of the microprocessor input, pulses of electrical current of fixed length are switched into the summing junction. The input is sampled by software in the microprocessor in order to determine its state. If the operational amplifier output is greater than the microprocessor's trip voltage, the software applies a fixed length pulse of positive current to the summing junction by applying 5 volts to the feedback resistor. The electrical current is equal to the summing junction voltage, which is approximately 2.50 volts, minus the feedback voltage, which is approximately 5.0 volts, divided by the feedback resistance. If the operational amplifier output is less than the trip voltage, the software in the microprocessor 120 applies a negative current pulse of the same length to the summing junction by applying 0 volts to the feedback resistor. This is repeated at a rapid rate to effectively cancel the current from the photodiode into the summing junction of the operational amplifier. A software counter within the microprocessor is used to monitor the number of positive charge pulses switched into the summing junction for a preselected number of total pulses which, in a preferred embodiment of the present invention, is 32,768 which represents the total number of distinct states of a 15 bit binary counter. This count of positive charge pulses switched into the summing junction is proportional to the average input current from the photodiode during the full sampling interval of 32,768 clock cycles. An offset current can be added to the summing junction to maintain the output within a convenient range. The offset current is provided by a resistor from a 5 volt supply to the summing junction. Although the delta-sigma method of analog to digital conversion is used in a preferred embodiment of the present invention, it should be understood that many other types of comparison methods can be used to compare the light intensity on photodiode 100 to the light intensity on photodiode 102.

With continued reference to FIG. 7, the other components and connections are well known to those skilled in the art. The use of the technique shown in FIG. 7 significantly reduces the cost of the associated circuitry by eliminating the need for many components while providing an accurate and efficient way to measure the light intensity received by the two photodiodes. The other components in FIG. 7 are identified in Table I below.

TABLE I

| Reference Numeral | Component or Value (Supplier) |
| --- | --- |
| 100 | VTP8350S (EG & G Vactec) |
| 102 | VTP8350S (EG & G Vactec) |
| 104 | NJU7002 (JRC) |
| 106 | 220pf |
| 110 | NJU7002 (JRC) |
| 112 | 22pf |
| 120 | PIC16C54 (Microchip) |
| 121 | 10KΩ |
| 122 | 10KΩ |
| 123 | 0.1f |
| 124 | 5.10KΩ |
| 125 | 20pf |
| 126 | 22MΩ |
| 127 | 1MΩ |
| 128 | 1MΩ |
| 129 | 10KΩ |
| 130 | 10KΩ |
| 131 | 0.1f |
| 132 | 22MΩ |

Figure 8:
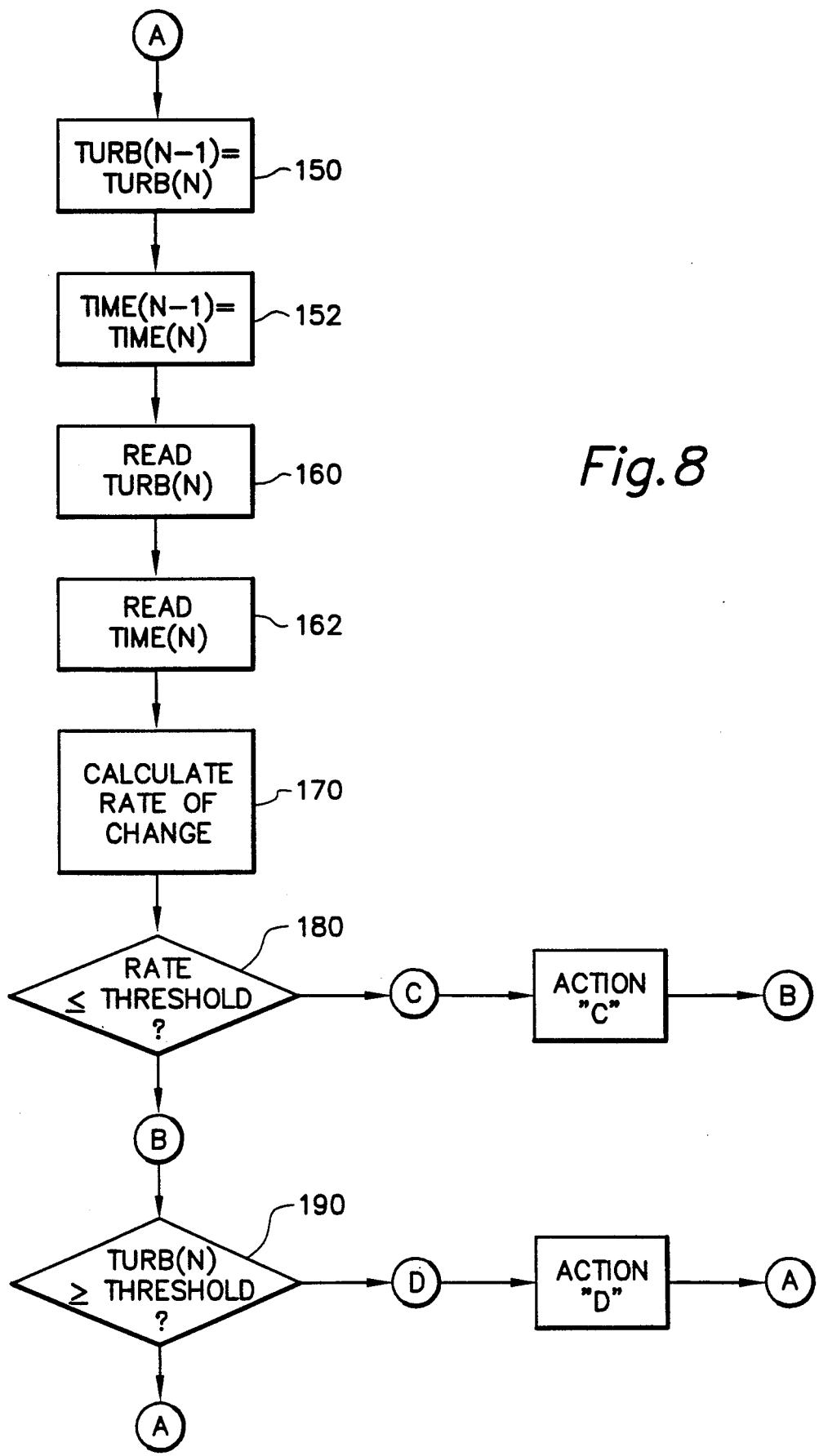
FIG. 8 shows an exemplary flow chart for a program segment used by a microprocessor associated with the present invention.

FIG. 8 illustrates an exemplary flow chart that represents a typical program segment that could be used in association with the present invention and be executed by the microprocessor 120 shown in FIG. 7 and discussed above.

It should be clearly understood that the flow chart in FIG. 8 is not intended to illustrate a required algorithm or a necessary method for performing the related functions. Instead, it is intended to illustrate one possible way that the microprocessor could monitor the values derived from the information provided by operational amplifiers 104 and 110. Beginning at step A in FIG. 8, the microprocessor would initially move the previous values of turbidity and time stored during a previous cycle of the program segment shown in FIG. 8. These steps are shown in function blocks 150 and 152. Next, the program would obtain new values for turbidity and time as illustrated by function blocks 160 and 162. When the program segment has the available information to compare the change in turbidity over a preselected change in time, it can calculate the rate of change of turbidity as indicated by function block 170. The rate of change of turbidity as a function of time can then be compared, as illustrated by function block 180, to a preselected threshold to determine whether or not the turbidity value of the fluid sample is increasing at an expected rate. If the rate is less than expected, the program jumps to point C and executes an appropriate action identified as "C". The next comparison performed by the program segment is represented as function block 190 and comprises a comparison of the absolute value of the turbidity determined at the most recent measurement to a predetermined threshold value. This comparison is intended to determine whether the turbidity is above an expected value which would indicate that particulate matter is appropriately being removed from the objects intended to be cleaned. In addition, a similar comparison could be made to determine whether the turbidity of the fluid has reached such a large magnitude that further efficient cleansing is determined to be improbable. If the absolute value of the turbidity taken at the last measurement does not meet the appropriate threshold, the program segment moves to step D and executes an action identified as "D". Notwithstanding the simplicity of the program segment flow chart shown in FIG. 8, it should be understood that the microprocessor 120 can compare the turbidity in its absolute magnitude to upper and lower thresholds and can additionally clarify the turbidity into one of several categories such as "clear", "moderately turbid", "turbid", "highly turbid", and so on. Once the fluid is appropriately categorized, the smart appliance can them determine the appropriate action to be taken, such as the addition of detergent or an increase in temperature. In addition, a smart appliance could also choose to empty the appliance of the highly turbid water and refill the appliance with clean water if this is deemed necessary. In addition, based on a comparison of the rate of change of turbidity over time to several threshold values, a smart appliance could determine the appropriate length of an initial wash cycle as a function of the rate of change of turbidity rather than as a function of time as is typically done in appliances known to those skilled in the art. This technique could detect the inappropriate beginning of a cycle when no dishes are in a dishwasher, could accurately determine the proper time to raise the temperature of water in a dishwasher if the rate of change of turbidity indicates that the soiled dishes are extremely greasy, and so on. The information provided by a turbidity sensor made in accordance with the present invention permits many alternative tactics to be employed by a smart appliance.

Figure 9:
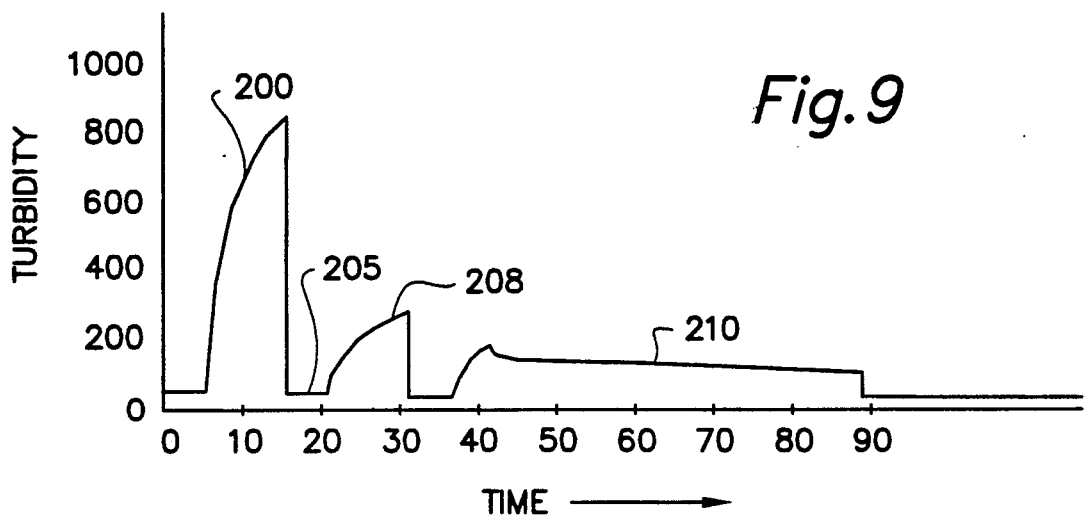
FIG. 9 shows the relationship between turbidity and time for an exemplary appliance.
Figure 10:
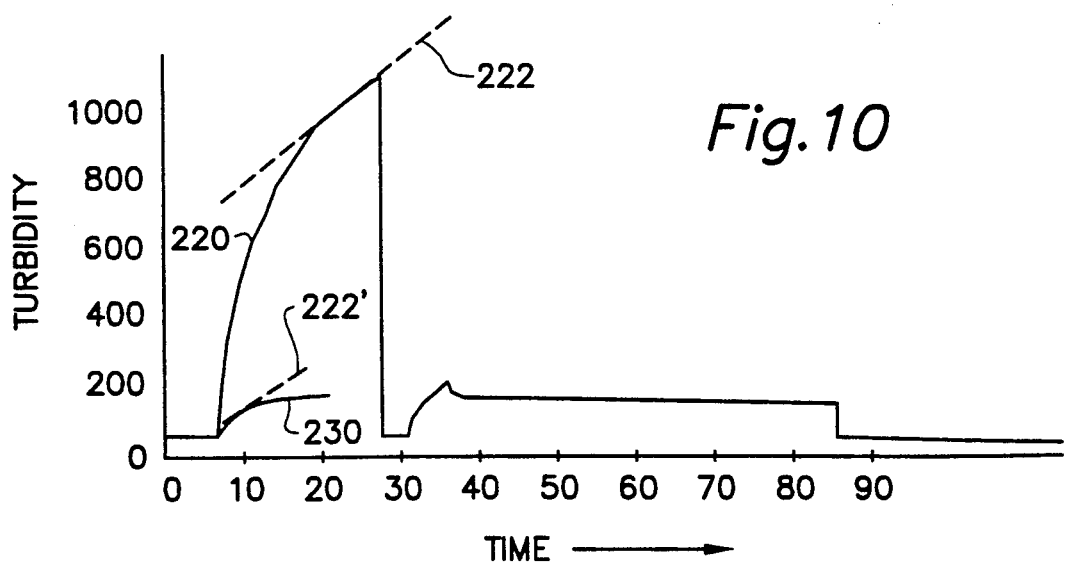
FIG. 10 shows the relationship between turbidity and time under several hypothetical conditions relating to an appliance.

FIG. 9 illustrates a hypothetical measurement of turbidity over time during a typical dishwashing cycle. As can be seen by the initial portion of curve 200, the cycle begins at time 5 and continues through time 15. During this period of time, the turbidity initially rises very quickly as particulate matter is removed from dishes and transported by the water flowing through the conduit of the turbidity sensor. As time continues, the rate of change of turbidity deceases although the absolute magnitude of turbidity continues to rise. In the example shown in FIG. 9, a timed cycle aborts the initial prewash cycle at time 15 and flushes the turbid water from the machine prior to filling the dishwasher with clean water. During the prewash from time 5 to time 15, soap is used and a significant amount of particular matter is removed from the dishes. Following a brief refilling procedure, from time 15 to time 20, the prerinse procedure begins. As can be seen the turbidity rises from its clear air value 205 as defined by curve 208. The timed cycle stops the prerinse portion of the procedure at time 30 and refills the appliance with water. The main wash cycle begins at time 35 with the turbidity again rising initially before leveling to a generally constant value. It is important to note the prewash cycle was aborted at time 15 as a function of time and not as a function of a parametric measurement. No attempt was made to determine whether a continuation of the prewash cycle beyond time 15 would be advantageous. Perhaps, if the prewash cycle was continued for a longer period of time while the turbidity continued to increase, the length of time of the main wash cycle, represented by reference numeral 210, could have been shortened. This could possibly save energy because the main wash cycle typically uses water at a much higher temperature than the two earlier cycles. With reference to FIG. 10, several possibilities of action in conjunction with the present invention are illustrated. First, it can be seen that the prewash cycle 200 and the prerinse cycle 208 shown in FIG. 9 have been combined into an initial operation identified by reference numeral 220 which is terminated when the rate of change of turbidity falls below a predetermined magnitude as represented by dashed line 222. As an example of a beneficial result that can be achieved by monitoring the rate of change of turbidity over time, curve 230 is shown in FIG. 10 to represent the possibility that an empty dishwasher or a dishwasher full of clean dishes was inadvertently caused to begin its washing cycle. Since no particulate matter would be removed from clean dishes and entrained in the fluid passing through the turbidity sensor, the turbidity would quickly level off as illustrated by curve 230 with only the dishwashing detergent increasing the turbidity of clear water by a very slight amount. When the rate of change of turbidity of curve 230 decreased below that illustrated by dashed line 222', the cycle can be aborted This would prevent the costly use of both time, water and power to clean dishes that are already clean or operate an empty dishwasher.

With continued reference to FIG. 10, the main wash cycle could possibly extend for a longer period of time within the overall total time represented in FIG. 9 or, alternatively, the main wash cycle could be significantly shortened as a function of the more efficient use of the prewash and prerinse cycles that are shown combined in FIG. 10. It should clearly be understood that FIGS. 9 and 10 are intended to show the hypothetical interaction between a turbidity sensor made in accordance with the present invention and a dishwasher or similar appliance. The illustrations in FIGS. 9 and 10 are not intended to show a preferred procedure or a required series of operations. The present invention is not limited to use in any particular manner or in conjunction with any specific algorithm or procedural method. The turbidity sensor of the present invention provides information that permits a smart appliance to use that information in many different ways to save both time and energy.

Although the present invention has been described in detail and illustrated with particular specificity to show a preferred embodiment of the present invention, it should be understood that alternative embodiments are within the scope of the present invention. For example, the method by which the light intensities are measured by the microprocessor illustrated in FIG. 7 is not the only way that this procedure can be accomplished. In addition, although the protrusions in the walls of the conduit are shown in and described as being four in number, it should be understood that other combinations and locations are possible within the scope of the present invention.

The embodiments of the invention in which an exclusive property or right is claimed are defined as follows:

1. A turbidity sensor, comprising:
   a light source;
   first and second light sensitive components disposed in light communication relation with said light source, said first light sensitive component being disposed to directly receive light emanating from said light source, said second light sensitive component being disposed to receive light emanating from said light source and scattered by particles suspended between said light source and said first light sensitive component, said first and second light sensitive components having first and second output signals, respectfully, which are representative of the light intensity received by their respective light sensitive components;
   means for determining a predefined relationship of said first and second output signals, said determining means comprising first means for canceling said first output signal with a first plurality of current pulses and second means for canceling said second output signal with a second plurality of current pulses, said determining means further comprising means for comparing said first and second plurality of pulses.

2. The turbidity sensor of claim 1, wherein:
   said predetermined relationship is a ratio of the numerical value of said first and second pluralities of current pulses.

3. The turbidity sensor of claim 2, further comprising:
   means for forming a value representing the turbidity of said fluid as a function of said ratio.

4. The turbidity sensor of claim 3, further comprising:
   a microprocessor which comprises said determining means and said forming means.

5. The turbidity sensor of claim 4, further comprising:
   means for calculating a rate of change of said turbidity representing value.

6. The turbidity sensor of claim 4, further comprising:
   means for comparing said turbidity representing value to a preselected magnitude.

7. A turbidity sensor, comprising:
   a light source;
   a first light sensitive component;
   a second light sensitive component, said first and second light sensitive components being disposed in light relation with said light source;
   means for passing a fluid between said light source and said first light sensitive component;
   first means for determining a first relationship between a first output from said first light sensitive component and a second output from said second light sensitive component, said first determining means comprising first means for canceling said first output signal with a first number of current pulses and second means for canceling said second output signal with a second number of current pulses, said first relationship being a ratio of said first and second numbers; and
   second means for determining a rate of change of said first relationship as a function of time.

8. The sensor of claim 7, wherein:
   said passing means comprises a tube, said light source and said first and second light sensitive components being disposed proximate transparent portions of the wall of said tube.

9. The sensor of claim 8, wherein:
   said first and second light sensitive components are photodiodes.

10. The sensor of claim 8, wherein:
    said light source is a light emitting diode.

11. A turbidity sensor, comprising:
    a fluid conduit;
    a light source disposed to transmit light along a first axis extending through said conduit;
    a first light sensitive component disposed on said first axis to receive light from said light source;
    a second light sensitive component disposed to receive light in a direction generally perpendicular to said axis from an internal portion of said conduit;
    means for comparing the light intensity received by said first and second light sensitive components and providing a signal representative thereof, said comparing means comprising first means for providing a first signal representative of said light intensity of said first light sensitive component and second means for providing a second signal representative of said light intensity of said second light sensitive component, said comparing means further comprising first means for canceling said first signal with a first number of current pulses and second means for canceling said second signal with a second number of current pulses, said comparing means further comprising means for determining a ratio of said first and second numbers.

12. The sensor of claim 11, further comprising: means for determining a turbidity value for a fluid disposed in said fluid conduit.

13. The sensor of claim 12, further comprising: means for calculating a rate of change of said turbidity value as a function of time.

14. The sensor of claim 12, further comprising: means for comparing said turbidity value to a preselected magnitude.

* * * * *